(12) United States Patent
Stormby

(10) Patent No.: US 9,421,125 B2
(45) Date of Patent: Aug. 23, 2016

(54) HEAD COOLER

(75) Inventor: Johan Stormby, Malmö (SE)

(73) Assignee: Dignitana AB, Lund (SE)

( * ) Notice: Subject to any disclaimer, the term of this patent is extended or adjusted under 35 U.S.C. 154(b) by 4 days.

(21) Appl. No.: 13/276,912

(22) Filed: Oct. 19, 2011

(65) Prior Publication Data

US 2012/0041526 A1    Feb. 16, 2012

Related U.S. Application Data

(62) Division of application No. 12/525,744, filed as application No. PCT/EP2008/051890 on Feb. 15, 2008.

(30) Foreign Application Priority Data

Feb. 15, 2007    (SE) .................................... 0700374-2

(51) Int. Cl.
  *F25D 23/12*    (2006.01)
  *A61F 7/10*    (2006.01)
  (Continued)

(52) U.S. Cl.
  CPC ........... *A61F 7/10* (2013.01); *A61F 2007/0004* (2013.01); *A61F 2007/0008* (2013.01); *A61F 2007/0056* (2013.01); *A61F 2007/0247* (2013.01); *A61F 2007/0287* (2013.01)

(58) Field of Classification Search
  CPC . F25D 2400/26; F25D 3/00; F25D 2303/082; F25D 2303/085; F25D 17/02; F25D 23/12; A41D 13/0053; A41D 13/005; A41D 2007/0002

USPC ............................ 62/259.3, 331, 530; 607/96
See application file for complete search history.

(56) References Cited

U.S. PATENT DOCUMENTS 4,138,743 A * 2/1979 Elkins et al. .................... 2/171.2
5,409,500 A   4/1995 Dyrek
(Continued)

FOREIGN PATENT DOCUMENTS

GB     2 418 614      4/2006
JP     6-270060       9/1994
(Continued)

OTHER PUBLICATIONS

Korean Office Action for corresponding Korean Application No. 10-2009-7018500 mailed Apr. 23, 2014 (8 pages).
(Continued)

*Primary Examiner* — Jonathan Bradford
*Assistant Examiner* — Elizabeth Martin
(74) *Attorney, Agent, or Firm* — Merchant & Gould P.C.

(57) ABSTRACT

A head cooler (10) comprises a thermal exchange cap (11) and an outer insulating cover (12) to be arranged on a patient's head. The cap (11) has a channel system (31, 32) for a cooling fluid forming an inside heat exchange surface to be applied on said head for cooling the head. The thermal exchange cap (11, 60) is adjustable and/or adaptable to compensate for a discrepancy in shape and size between the inside surface of the head cooler (10) and the head. The head cooler (10) may further comprise an eyebrow cooler (140) for cooling the area of the eyebrows. The head cooler (140) is used in medicine. A method for preventing hair loss of a patient is provided by arranging the head cooler (10) on the head of said patient.

13 Claims, 12 Drawing Sheets

(51) Int. Cl.
*A61F 7/00* (2006.01)
*A61F 7/02* (2006.01)

(56) References Cited

U.S. PATENT DOCUMENTS

| | | | | |
|---|---|---|---|---|
| 6,126,680 | A * | 10/2000 | Wass | 607/96 |
| 6,156,059 | A | 12/2000 | Olofsson | |
| 6,178,562 | B1 | 1/2001 | Elkins | |
| 6,183,501 | B1 | 2/2001 | Latham | |
| 6,277,143 | B1 | 8/2001 | Klatz et al. | |
| 6,312,453 | B1 * | 11/2001 | Stefanile et al. | 607/109 |
| 2002/0058976 | A1 | 5/2002 | Lee | |
| 2008/0097560 | A1 * | 4/2008 | Radziunas et al. | 607/104 |
| 2010/0083421 | A1 * | 4/2010 | Cho | 2/171.2 |

FOREIGN PATENT DOCUMENTS

| | | |
|---|---|---|
| JP | 2001-502207 | 2/2011 |
| WO | WO 98/16176 | 4/1998 |
| WO | WO 00/03666 | 1/2000 |

OTHER PUBLICATIONS

International Search Report for International Application No. PCT/EP2008/051890 mailed Jul. 11, 2008 (4 pages).

International Preliminary Report on Patentability for International Application No. PCT/EP2008/051890 mailed May 15, 2009 (11 pages).

* cited by examiner

HEAD COOLER

This application is a Divisional of U.S. Ser. No. 12/525,744, filed 4 Aug. 2009, which is a National Stage Application of PCT/EP2008/051890, filed 15 Feb. 2008, which claims benefit of Serial No. 0700374-2, filed 15 Feb. 2007 in Sweden and which applications are incorporated herein by reference. To the extent appropriate, a claim of priority is made to each of the above disclosed applications.

TECHNICAL FIELD

The present invention relates to a head cooler to be arranged at the head of a person undergoing treatment of cytostatics.

BACKGROUND OF THE INVENTION

A human being undergoing treatment with cytostatics (chemotherapy) or similar treatment often suffers from loss of hair. By maintaining, during the treatment, a low temperature on/at/of the hairy region, usually the scalp, such a loss can be eliminated or substantially reduced.

A head cooler disclosed in U.S. Pat. No. 6,156,059 comprises a head cover to be placed over a human scalp for enclosing the patient's head and neck. Flow passages, through which a cooling fluid is flown, are provided in the cover which forms an inside heat exchange surface to be applied against the scalp for cooling the scalp. A temperature sensor is mounted in connection with each flow passage for registering the local temperature.

The size and shape of heads of different patients may vary a lot. If the head cooler is too large or too wide, a gap may be formed between the heat exchange surface and the head. Then, the cooling of the scalp may be jeopardized, since the heat exchange surface is not held in contact with the scalp over the entire surface thereof. As a consequence the cooling efficiency will be reduced in the area of the gap resulting in loss of hair.

It is proposed according to the Japanese Patent Abstract of Patent Application No. 6270060 to mount to the inside surface of the head cover a plurality of bag bodies to which a pressure fluid is supplied in order to press a heat exchange surface against the patient's head and neck for cooling the scalp.

A drawback with currently used head coolers is that the head cover is not easily adaptable to the size and/or shape of the patient's head and neck, which may result in a too low or an impaired cooling efficiency.

Another disadvantage is that the currently presented head coolers do not involve the cooling of the eyebrows or the region of the eyebrows. Loss of the eyebrows is also considered to be a problem for patients undergoing treatments with cytostatics.

DISCLOSURE OF THE INVENTION

An object of the present invention is to eliminate or alleviate at least one of the drawbacks mentioned above, which is achieved by assigning to the device the characteristics according to claim 1.

According to one aspect of the invention, there is provided a head cooler comprising a thermal exchange cap to be arranged on the head of a patient, and at least one flow passage system for a cooling fluid provided in the thermal exchange cap forming an inside heat exchange surface to be applied against the head for cooling of the head. The thermal exchange cap is adaptable and/or adjustable to compensate for a discrepancy, if any, as to shape and size between the inside surface of the head cooler and the head.

The head cooler further comprises an outer insulating cover made of a heat insulating material, e.g. also elastic, which encloses the thermal exchange cap. The head cooler comprises means for filling up, by the supply of a fluid heat conducting material, a gap between the inside surface of the thermal exchange cap and the head.

According to one embodiment, the thermal exchange cap is partitioned into sections that are engageable at adjacent edge portions. The sections are mutually overlapping and are slidable against each other, and are oppositely bevelled in the transverse direction. Each section has at least one flow passage system for the cooling fluid. The cross sections of the flow passages are wedge shaped, circular, semi circular, rectangular, elliptical, square or of any other shape. The partitioned sections have a common inlet and/or outlet flow passage or a separate inlet and/or outlet flow passage for the cooling fluid. A flow passage extends along each side of the partitioned sections, which converge to a common location on the thermal exchange cap, preferably at the top, and extend into an opening on said location.

The filling up means comprises at least one external connection on the thermal exchange cap communicating with a space between the inside of the thermal exchange cap and the scalp.

According to another embodiment the head cooler further comprises an inner head cover consisting of a flattened bag of flexible material, which can be inflated, forming a lining on the inside of the thermal exchange cap. The bag forms a single cavity or multiple cavities. At least one valve or other means, such as a tube, is provided between a cavity of the bag and the flow passage system for supplying cooling fluid from said system to the bag cavity/cavities.

Means are provided for controlling the flow of the cooling fluid. A connection is provided for supplying air or a gas or a gas mixture (under pressure) to the flow passage system or to the cavity or cavities to evacuate the cooling fluid from the bag.

According to an alternative embodiment, the head cooler is complemented by an eyebrow cooler comprising a flattened bag of flexible material, which can be inflated. The bag forms a single cavity or multiple cavities, at least one valve or other means, such as a tube, is provided between the cavity of the bag and a flow passage system for supplying a cooling fluid from said system to the bag cavity/cavities.

According to a second aspect of the invention, a use of a head cooler is provided for preventing hair loss during chemotherapy treatment.

Further objects, features and advantages of the present invention will appear from the following detailed description, from the attached drawings as well as from the dependent claims.

BRIEF DESCRIPTION OF THE DRAWINGS

In order to explain the invention, a number of embodiments of the invention will be described below with reference to the drawings, in which.

Same reference numerals have been used to indicate the same parts in the figures to increase the readability of the description and for the sake of clarity.

DESCRIPTION OF EMBODIMENTS OF THE INVENTION

Figure 1:
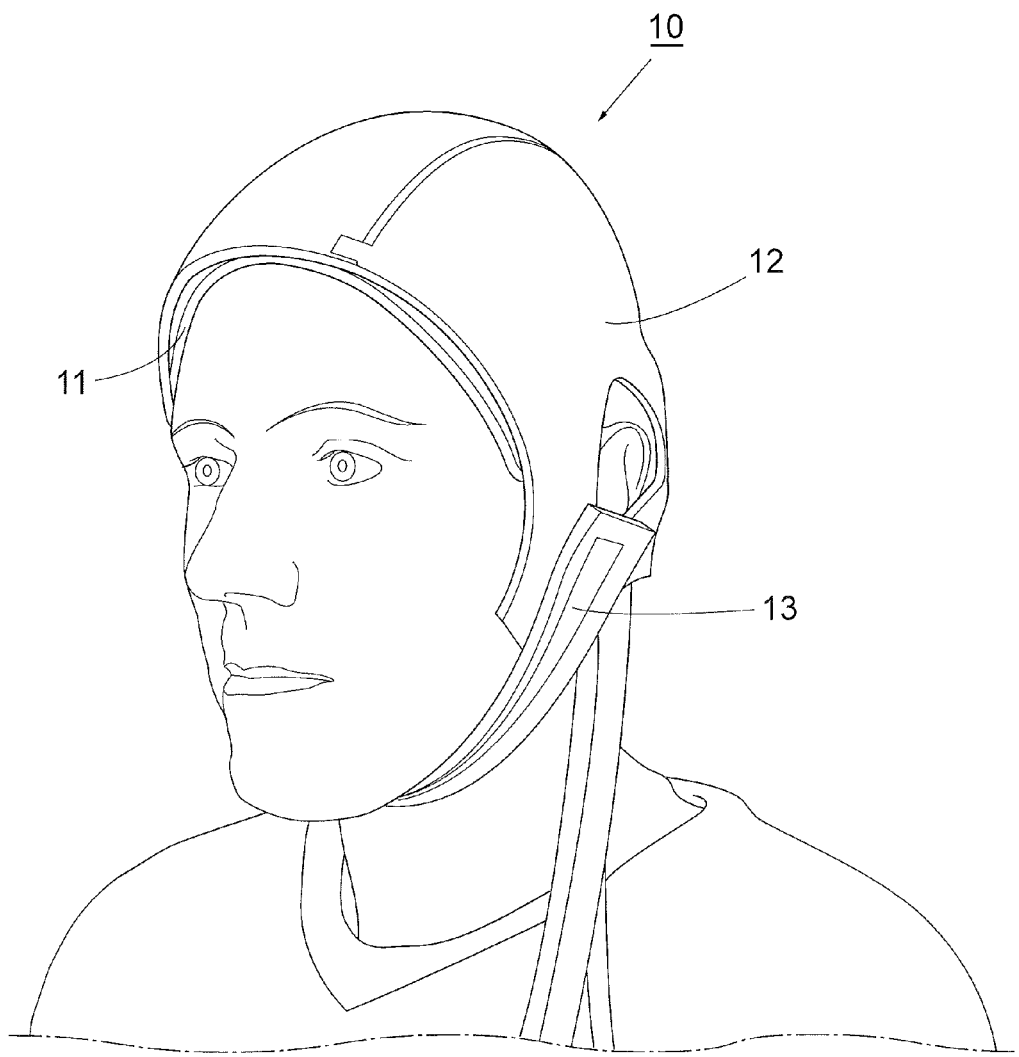
FIG. 1 is a perspective view of a head cooler according to the invention, which is in use with a patient.
Figure 2:
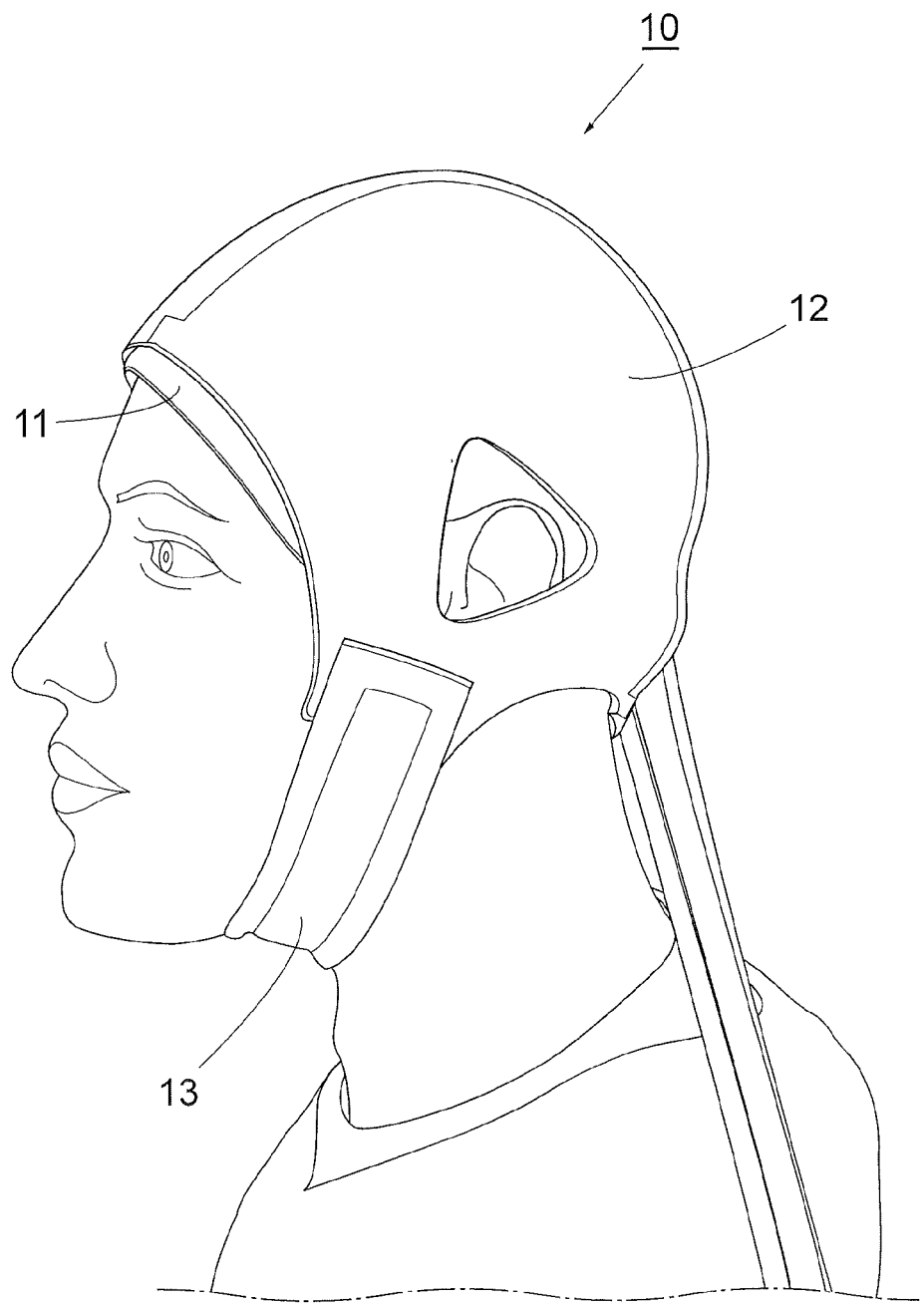
FIG. 2 is a side view of the head cooler in FIG. 1.

A head cooler 10 according to one embodiment of the invention comprises a thermal exchange cap 11 and an outer insulating cap 12, as shown in FIGS. 1 and 2. The outer insulating cover is fitted over the thermal exchange cap to stabilize the cap on the patient. The outer cover is made of a heat insulating and elastic material, e.g. neoprenes of the type used in diving suits, to heat insulate the thermal exchange cap against the surroundings.

A chinstrap 13 can improve the stabilization of the outer insulating cover. A first end of the strap is attached to the lower margin at one side of the outer cover and a second end of the strap, which is provided with a Velcro type fastener for adjustable and releasable connection, is attached at the other side of the outer cover.

Figure 3:
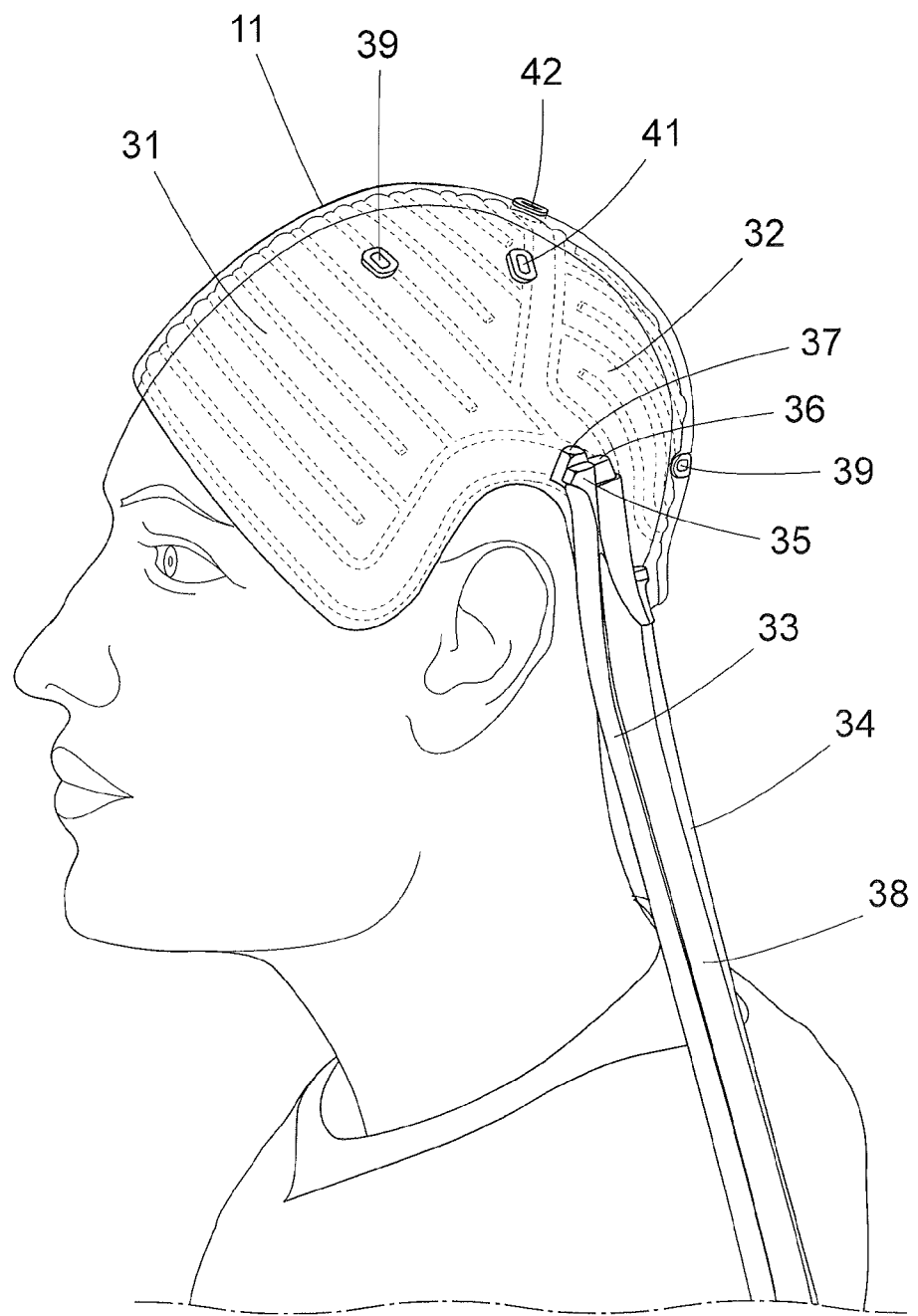
FIG. 3 is a side view of the head cooler in use, but shown without the outer insulating cover.
Figure 4:
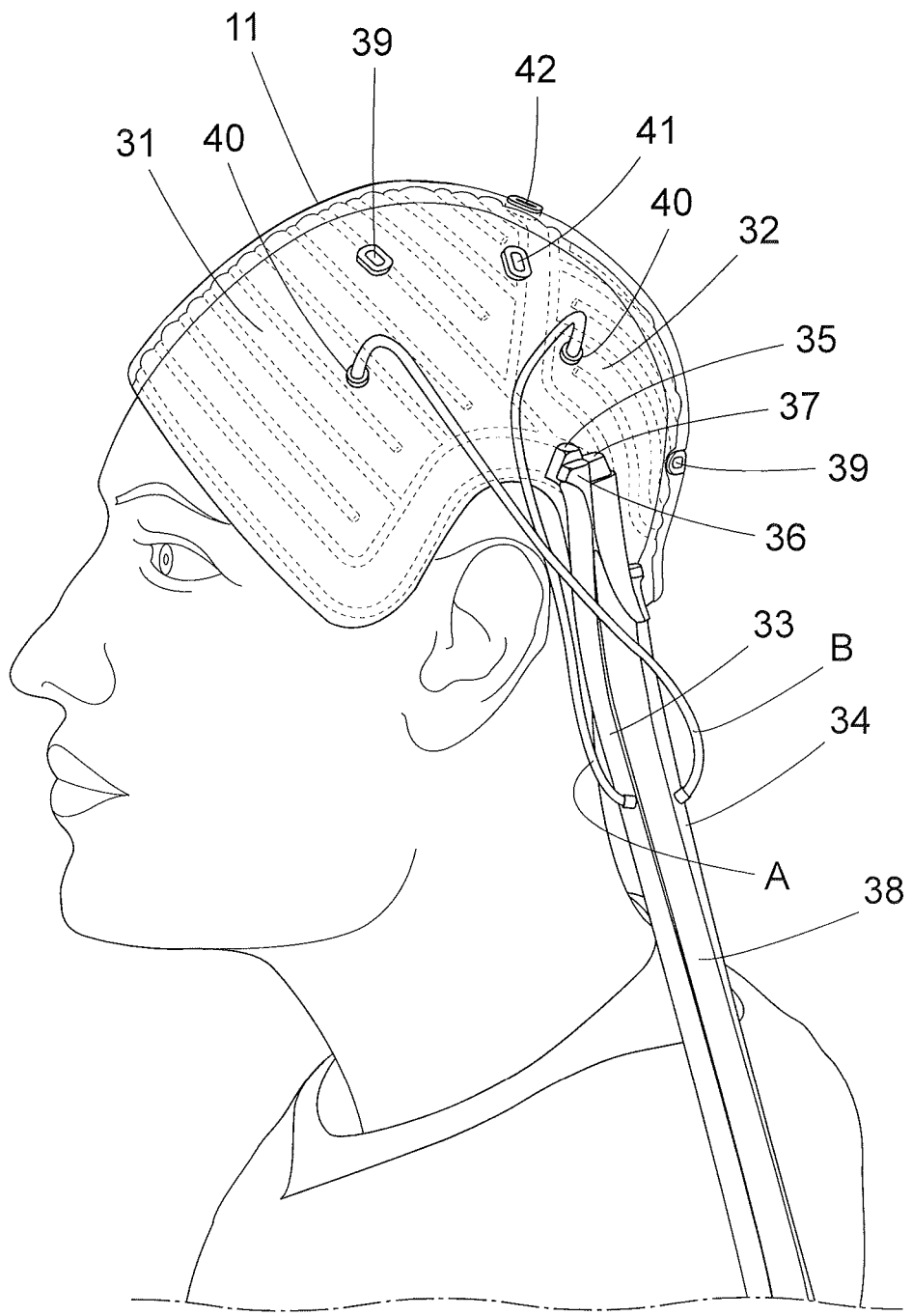
FIG. 4 is the head cooler in FIG. 3 provided with additional tubes.
Figure 5:
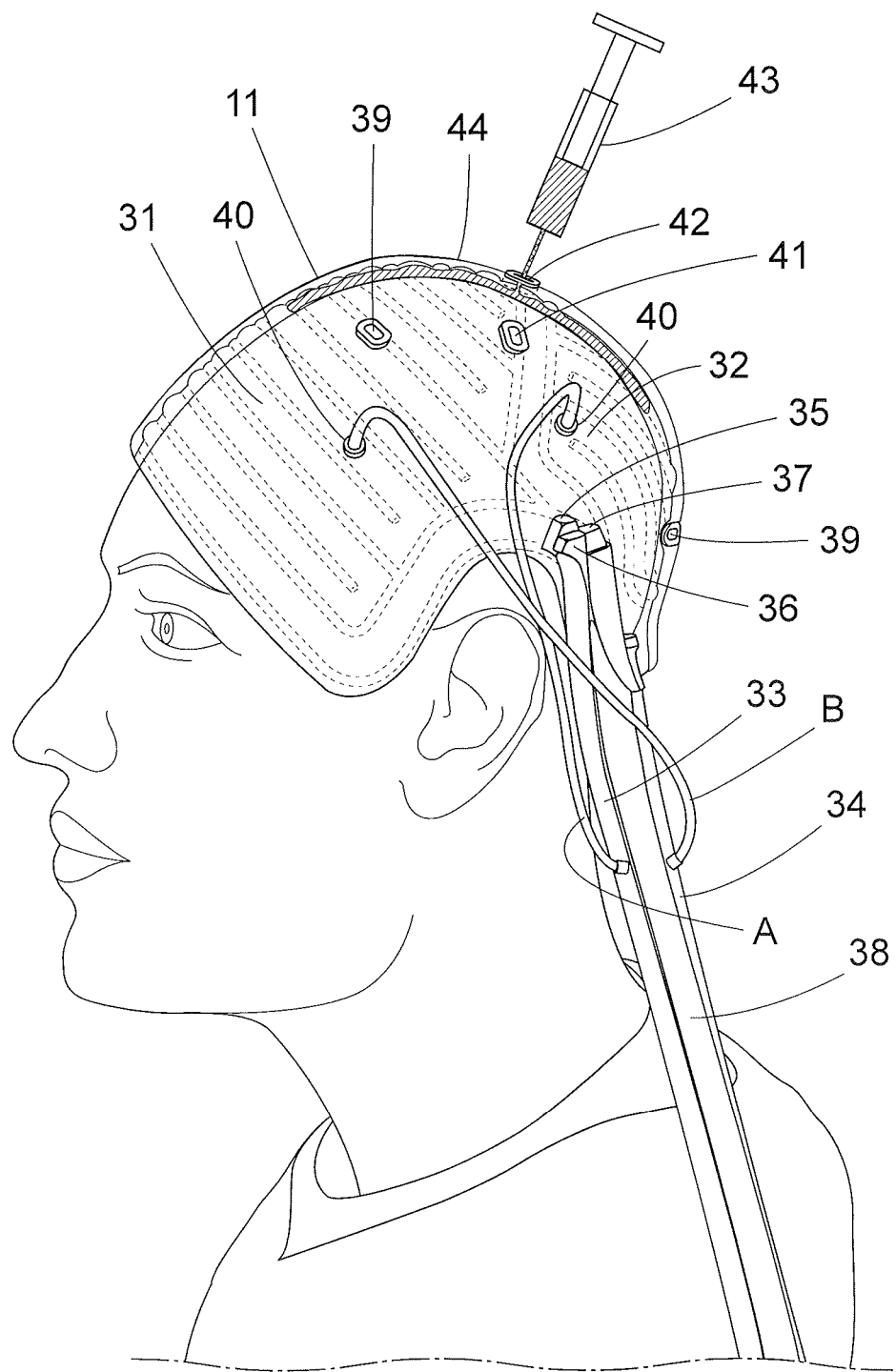
FIG. 5 is a side view of the head cooler in FIG. 4 during injection of a fluid filling up a gap between the heat exchange surface of the thermal exchange cap and the scalp.

FIGS. 3, 4 and 5 show the head cooler without the outer insulating cover. The thermal exchange cap 11 is made of a flexible and preferably elastic material, such as silicone rubber of medical grade, to fit tightly over the head and neck of a patient. The thermal exchange cap forms internal partitions, which can be made from the material of the cap and which define two channel systems, a first one 31 extending over the forward portion of the thermal exchange cap and a second one 32 extending over the neck portion of the thermal exchange cap. Flexible hoses 33 and 34 are connected to inlets 35 and 36 of the cap, communicating with the channel systems 31 and 32, respectively. An outlet 37, communicating with the both channel systems 31 and 32, is connected with a flexible hose 38. The hoses 33, 34, 38 are connected with an external device (not shown) for circulating a cooling fluid through the channel systems, and means are provided for controlling the flow of the cooling fluid. Since the front part of the head emits more heat than the back part of the head, the flow in the forward portion, i.e. in the first channel system 31, may be higher than in the neck portion, i.e. in the second channel system 32. Alternatively, the temperature of the cooling liquid may be lower in the forward portion than in the neck portion.

The two channel systems 31 and 32 may be of a meander shape, a labyrinth shape, and/or maze shape, as disclosed in FIGS. 3 to 6. These shapes maximize the exchange surface against the head. It is also preferable to have the substantial extension of the channel systems 31 and 32 in the direction around the head, i.e. in a plane substantially perpendicular to the anteroposterior axis of the patient. In this way blood vessels in the head, having a substantial anterior direction, will be crossed by the flow of cooling liquid in an early phase of the cooling procedure, while the cooling ability of the cooling liquid still is high, assuring that substantially all the blood will be heat exchanged with the head cooler. Also, it is believed that the pressure to be applied may be minimized, since the cooling liquid only has to travel once from the inlet to the top of the head in a net anterior direction, i.e. upwards during use.

It is also preferable to have the inlets 35 and 36 in the posterior end of the head cooler, such as disclosed in FIG. 3. Thus, the cooling liquid circulating in the head cooler will substantially move in a plane substantially perpendicular to the anteroposterior axis of the patient, while traveling from the posterior end to the anterior end of the head cooler by the stepwise elevation in the meander shaped, labyrinth shaped, and/or maze shaped channel systems 31 and 32. In this way the warm blood to be cooled will be heat exchanged with cooling liquid of high cooling ability in a net parallel heat exchange, resulting in a more higher heat exchange effect posteriorly. A high heat exchange effect posteriorly is beneficial, since it then can be assured that the blood entering the scalp has an initial high temperature drop.

The present invention may been realized by moulding the head cooler in two pieces of the flexible and preferably elastic material, such as silicone rubber of medical grade, wherein a first piece, for example the piece intended to be closest to the skull during use, may be moulded with the channel systems by forming ribs shaping the channel systems, while a second piece, for example the piece intended to be closest to the surroundings during use, may be a substantially flat piece. Thereafter, the first and second pieces are attached to each other by for example providing the ribs on the first piece with glue and then apply the second piece thereon, whereby the first piece and the second piece will be glued together while forming the channel systems 31 and 32 in space in between the ribs. It has up to this point not been possible to shape channel systems in head coolers in this way, whereby it has not been possible to manufacture head coolers with integrated meander shaped, labyrinth shaped, and/or maze shaped channel systems.

Any other arrangement than that described herein can be provided for circulating the cooling fluid through the channel systems, for example the channel systems can have separate outlets, or the two channel systems can be interconnected, thus forming a single system having a single inlet. Alternate embodiments can comprise one system or more than two systems. The cross sections of the flow passages of the channel systems can be of any shape, e.g. circular, semi circular, elliptical, triangular, rectangular, square or wedge Shaped. The thermal exchange cap, as shown in FIGS. 3 and 4, comprises two hollow studs 39 for insertion of temperature sensors for measuring the temperature on or close to the surface of the scalp in the regions of the channel systems 31 and 32, respectively. The sensors can be operatively connected with the device circulating cooling fluid through the channel systems for controlling the flow of cooling fluid and the temperature of the related region of the scalp in dependence of the temperature sensed.

The cap comprises an additional hollow stud 41 for the insertion of a safety temperature sensor for measuring the temperature on or close to the surface of the scalp. The safety temperature sensor senses the temperature in an independent position on or close to the scalp, in relation to above mentioned stud(s) 39, and is operatively connected with the device for circulating cooling fluid, in order to shut off said device, e.g. if the temperature on or close to the scalp sinks below a set temperature to avoid frost injury.

In an alternate embodiment the studs may be omitted, or only one stud or more than two studs may be provided.

As explained above, there may be a discrepancy between the size and shape of the patient's head and neck and the size and shape of the thermal exchange cap, resulting in a gap between the inside of the heat exchange cap and the scalp. This may jeopardize the efficiency of the cooling of the patient's scalp, since the inside surface of the cap, i.e. the heat exchange surface, partially is not in contact with the surface of the scalp.

In order to allow compensation for the discrepancy in shape, there can be provided, on the crown of the thermal exchange cap, a further hollow stud 42 to which an injection syringe 43 can be connected for the injection of a heat conducting material 44 into the gap, as illustrated in FIG. 4. Suitable materials for this purpose are e.g. gels, hydro gels, liquids, such as water or cooling liquid, and pastes. The material can include an additive, for example a blood vessel contracting substance, such as nicotine, and/or a heat conducting material, such as a salt or a metal. The stud 42 can be located in another position than that shown in FIG. 4, and additional hollow studs 40 can be provided in other positions on the cap, e.g. for inserting additional tubes A, B, which will be explained below.

Figure 6:
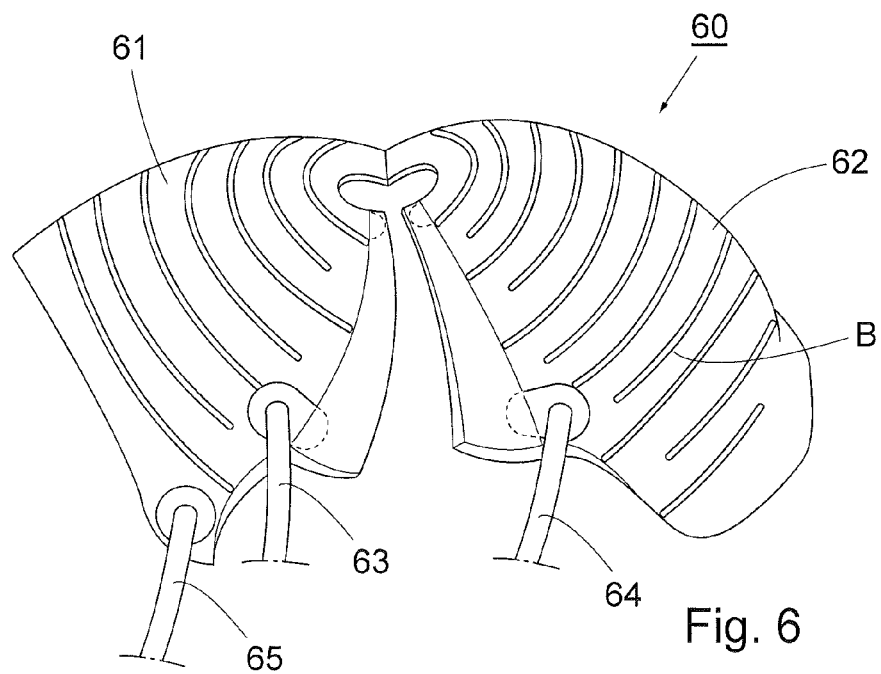
FIG. 6 is a side view of a partitioned thermal exchange cap, wherein the sections are shown separated.
Figure 7:
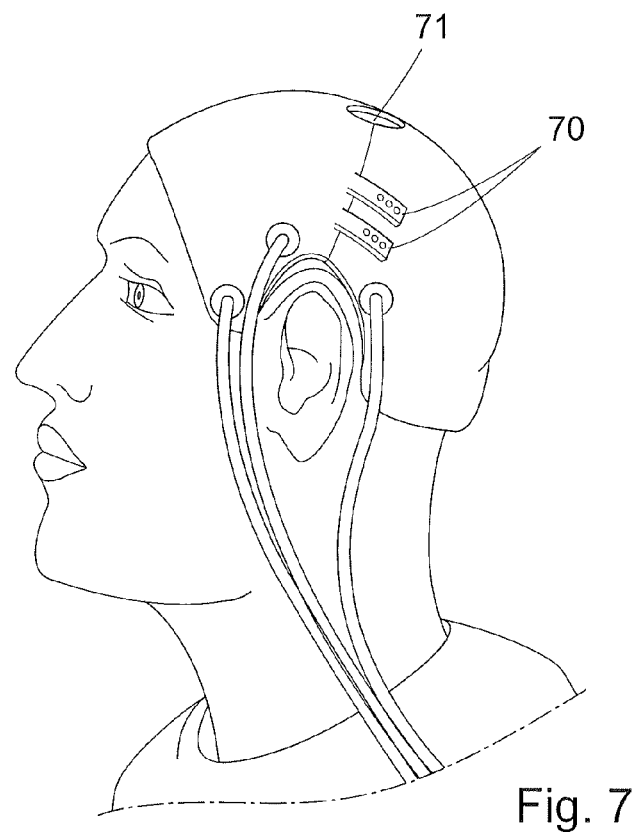
FIG. 7 is a side view of the cap in FIG. 6 with the sections closed and interconnected.
Figure 8:
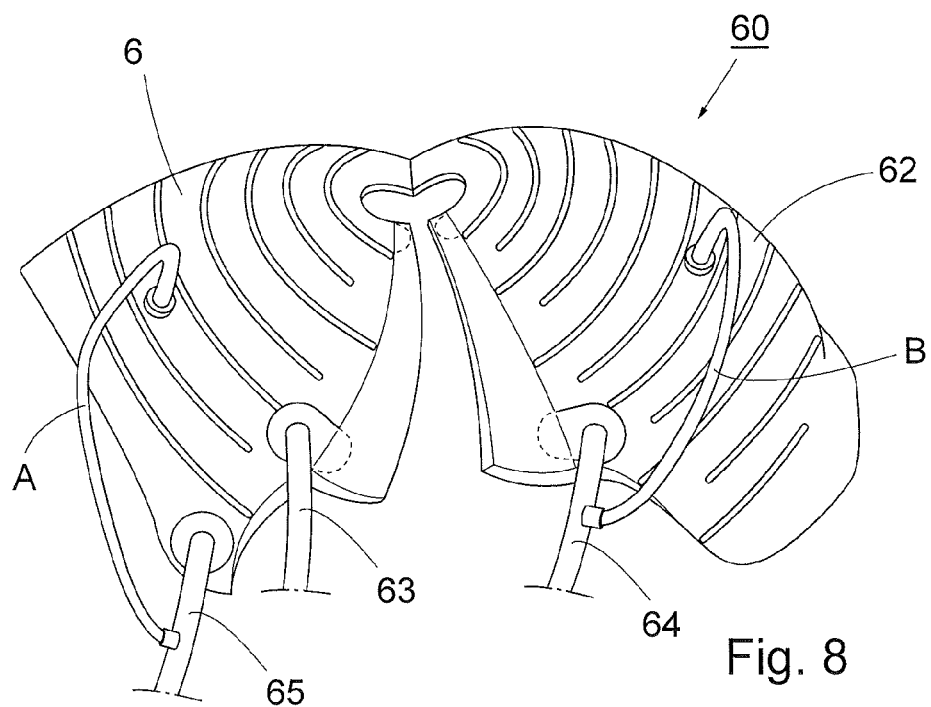
FIG. 8 shows the thermal exchange cap in FIG. 6 provided with additional tubes.
Figure 9:
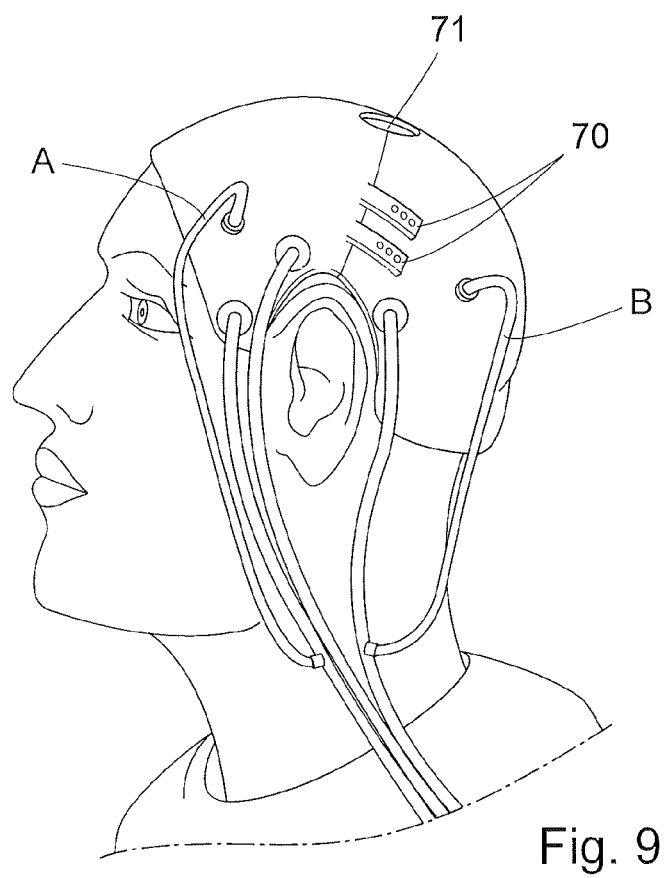
FIG. 9 shows the thermal exchange cap in FIG. 7 provided with additional tubes.

To compensate for the discrepancy in size of head and neck, another embodiment of the thermal exchange cap 60 is provided, as shown in FIG. 6. The thermal exchange cap 60 is partitioned into two sections 61 and 62, and has mutually overlapping edge portions sliding against each other. The edge portions may be oppositely bevelled in the transverse direction thereof to reduce the material thickness at the overlapping site. The cap has inlets 63 and 64, which are arranged to the sections 61 and 62, respectively, and are in communication with flow channels for circulating the cooling fluid through the flow channels, as described above. An outlet 65 is provided for recirculation of the cooling fluid back to the cooling device. A device 70 is arranged for interlocking the sections of the cap, taking into account different head sizes and also for the purpose of forming the smallest possible air gap between the inside surface of the thermal exchange cap and the patients head. A hole or an opening 71, for example substantially circular or elliptical, is provided on the top of the cap, or at the point where the sections converge, to avoid a cone-shaped deformation of the cap.

To further improve the adaptation of the thermal exchange cap to the size of the head and neck of the patient, the flow passages from the inlet may be arranged along each defined side of the partitions of one or more sections, from the lower margin of the cap to the top of the cap, or further to the opposite lower margin, to avoid one or more gaps between the thermal exchange cap and the scalp at arrangement on the head of the patient. The flow passages may have a wedge shaped, a rectangular or a semi circular cross section having the base member or broadest member arranged against the head of the patient to improve the adaptation of the cap to the head.

According to alternative embodiments, the thermal exchange cap may be partly partitioned into one section or fully partitioned into several sections, which converge to a point and extend into an opening. Furthermore, each section may have one or several inlets and one or several outlets, and may have multiple channel systems, which may be separated from each other or interconnected using or not using same inlet(s) and/or outlet(s).

Supplementary holes, not shown, may be provided on the inside and/or outside of the thermal exchange cap 11 and 60, which will be explained in detail below. The holes may be provided with valves or tubes.

The thermal exchange cap according to any of the described embodiments may have elevated ridges (not shown) arranged on the exterior surface in order to form air gaps between the thermal exchange cap and the outer insulating cover 12, when arranged on the head of a patient.

Figure 12:
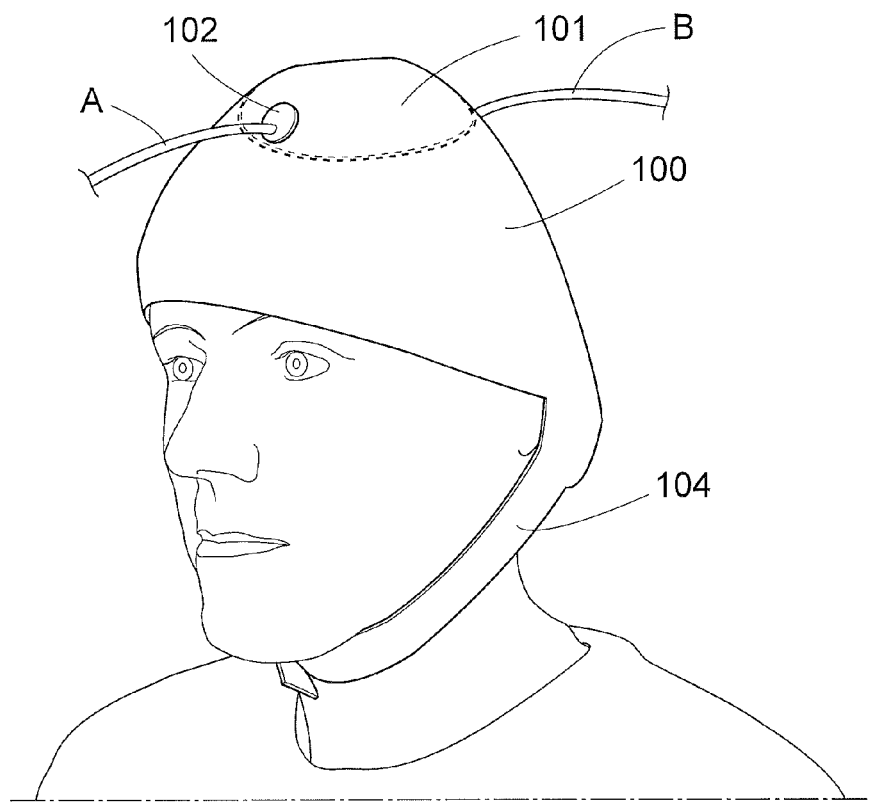
FIG. 12 shows the inner head cover in FIG. 10 provided with additional tubes.
Figure 13:
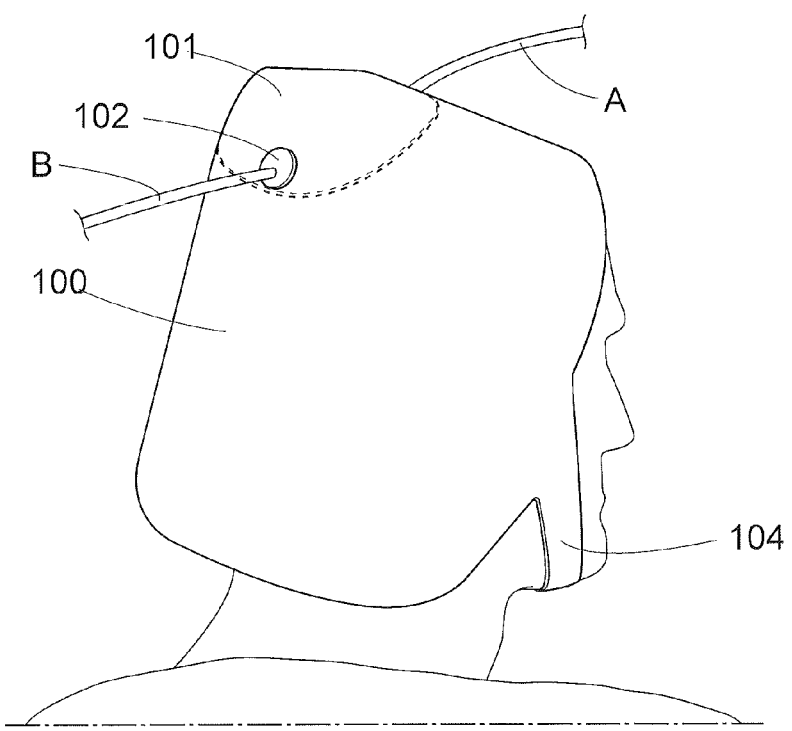
FIG. 13 shows the inner head cover in FIG. 11 provided with additional tubes.

To further improve the cooling efficiency of the head cooler, there is provided an inner head cover 100 to be arranged on the patients head under the thermal exchange cap 11, 60, as a lining thereof. The inner head cover comprises a flattened bag made of one sheet, or two or several superposed sheets, of flexible elastic or not elastic plastic material or other material, which is/are welded, glued, stitched or in any other way joined forming one cavity or multiple separated cavities in the inner head cover. One or several holes 102, provided or not with valves 103, is/are arranged into the cavity or the multiple cavities to allow inlet of a circulating cooling fluid via tubes A, B, as shown in FIGS. 12 and 13, from a cooling fluid source for filling up the cavity or cavities in order to minimize the air gap between the patients head and the thermal exchange cap 11, 60, and hence for improving the thermal conduction between the patients head and the thermal exchange cap. Similarly, the holes 102 provided with or without valves or tubes A, B allow outlet of the cooling fluid for recirculation of the fluid back to the source.

Figure 10:
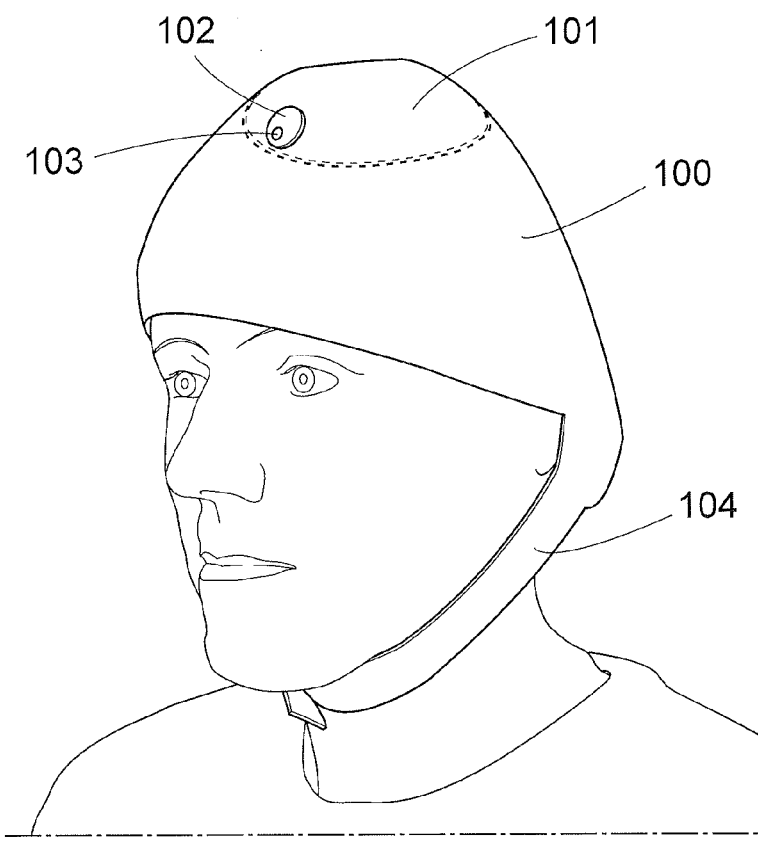
FIG. 10 is a frontal perspective view of an inner head cover having a cavity provided at the top thereof.
Figure 11:
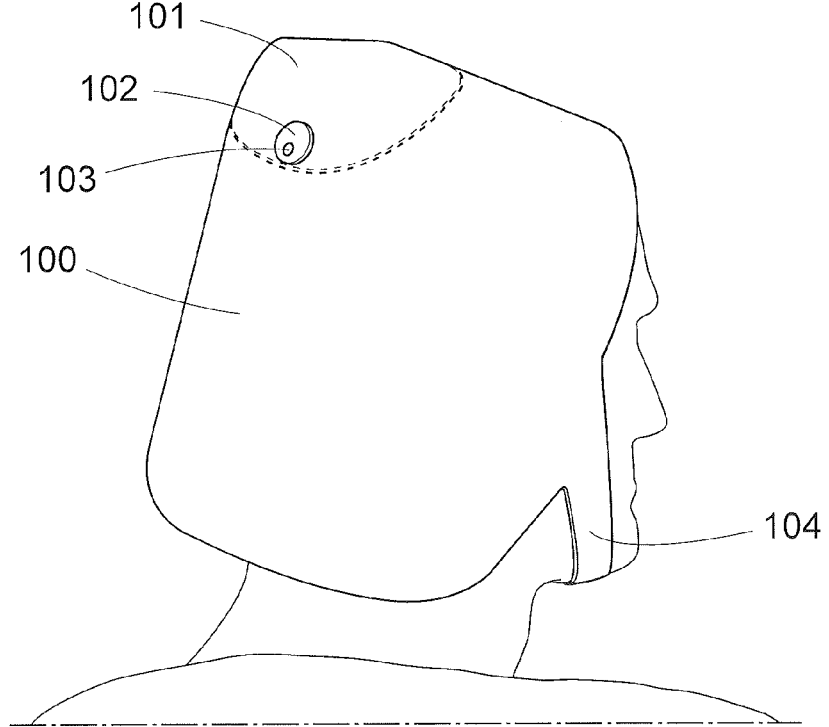
FIG. 11 is a perspective view of the inner head cover of FIG. 10 from behind.

FIGS. 10 and 11 show the inner head cover 100 having a cavity 101 formed on the top thereof, wherein the cavity has at least two holes 102 provided with valves 103. Alternatively, tubes A, B may be arranged to the holes 102, as illustrated in FIGS. 12 and 13. A chin strip 104 of plastic material is arranged to the lower margin of the inner head cover for securing the inner cover to the patient.

In a further embodiment the cavity (or cavities) of the inner head cover 100 communicates (communicate) with the channel systems of the thermal exchange cap 11, 60 by the holes 102, which are connected to the additional holes 40 of the thermal exchange cap 11, 60 via the valves 103, thus the channel systems of the cap supply the cooling fluid to the inner head cover. The supply can be performed continuously during the treatment, or instantly before start of the treatment. In the latter case the valves will be closed when the cavity/cavities is/are filled. Alternatively, the cavity is filled with cooling fluid via tubes A, B connected to at least one of the hoses 33, 34, 38, or by injecting the fluid by a syringe or another means. Furthermore, the cavity or cavities can be filled with a cooling fluid before placing the cover on the head of a patient. The valves 103 may be of different types, for example pressure regulating valves, non return valves, etc.

One or several additional sealable or not sealable openings may be provided on the inner head cover for injection of a gel or other fluid having appropriate viscosity in order to minimize air gaps between the thermal exchange cap and the patient's head, for further improving the thermal conduction there between.

A connection device for an emptying tube or emptying valve may be coupled to the hoses 34, 35, 38 mounted to the channel systems of the thermal exchange cap 11, 60, in order to inflate the cavity/cavities of the inner head cover by air or gas or a gas mixture of atmospheric pressure or overpressure, or deflate the cavity/cavities by vacuum, in order to evacuate the remaining cooling fluid of the cavity/cavities after finished treatment. In some cases it may be possible to evacuate the cavity/cavities simply by the channel systems via a tube using gravitation.

In the embodiments described, there are several flow passages or channels in the thermal exchange cap for the cooling fluid, but it is also possible to have a single space or several spaces interconnected with each other, through which space/spaces the cooling fluid is passed between the fluid inlet and the fluid outlet.

Figure 14:
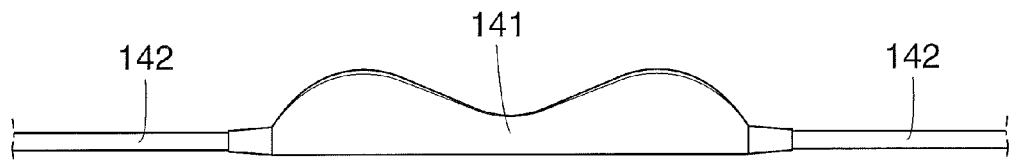
FIG. 14 is a frontal schematic view of an eyebrow cooler.
Figure 15:
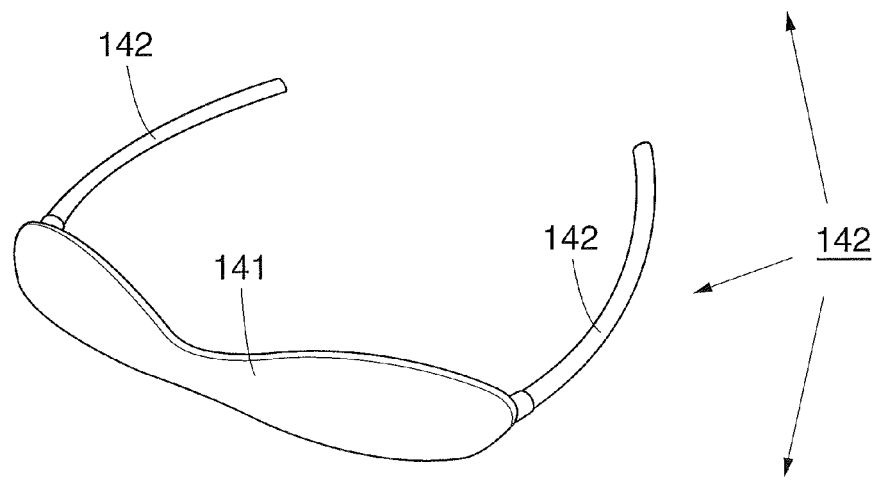
FIG. 15 is a perspective view of the eyebrow cooler in FIG. 14.
Figure 16:
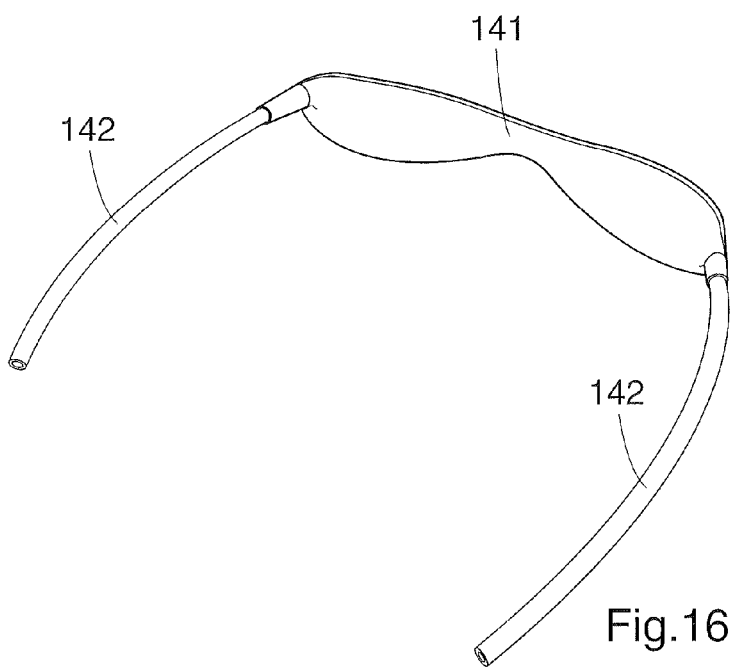
FIG. 16 is a perspective view of the eyebrow cooler in FIG. 15 from behind.

The head cooler according to the embodiments described above can be complemented with an eyebrow cooler 140 for cooling the eyebrows of the patient, as shown in FIGS. 14, 15 and 16. The eyebrow cooler is made of a flexible and preferably elastic material, such as silicone rubber or plastic material of medical grade, to be adapted closely to the forehead of a patient. The eyebrow cooler comprises a flattened bag made of one sheet, or two or several superposed sheets, which is/are welded, glued, stitched or in any other way joined forming one cavity or multiple cavities. Hoses 142 are connected to the eyebrow cooler at a first end, and are in communication with the cavity or cavities to allow inlet and outlet of a circulating cooling fluid. The second ends of the hoses 142 can be connected to the hoses 33 and 34, respectively, which are coupled to a cooling fluid source, or the ends can be coupled directly to the cooling source. The eyebrow cooler may comprise one or several hollow stud(s) (not shown) for the insertion of one or more temperature sensors for controlling the temperature at the area of the eyebrow cooler 140.

Figure 17:
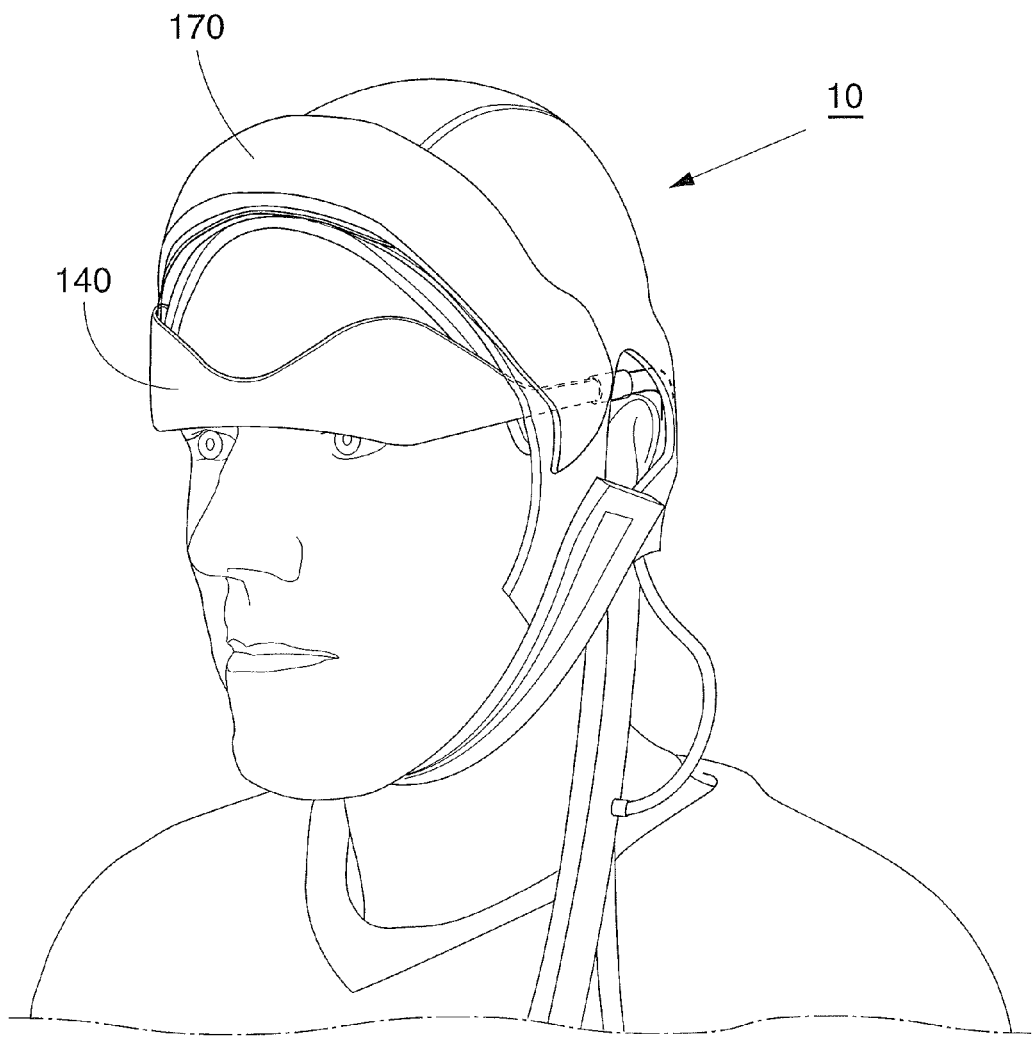
FIG. 17 shows the head cooler in FIG. 1 provided with an eyebrow cooler and an insulating eyebrow cover in raised position.
Figure 18:
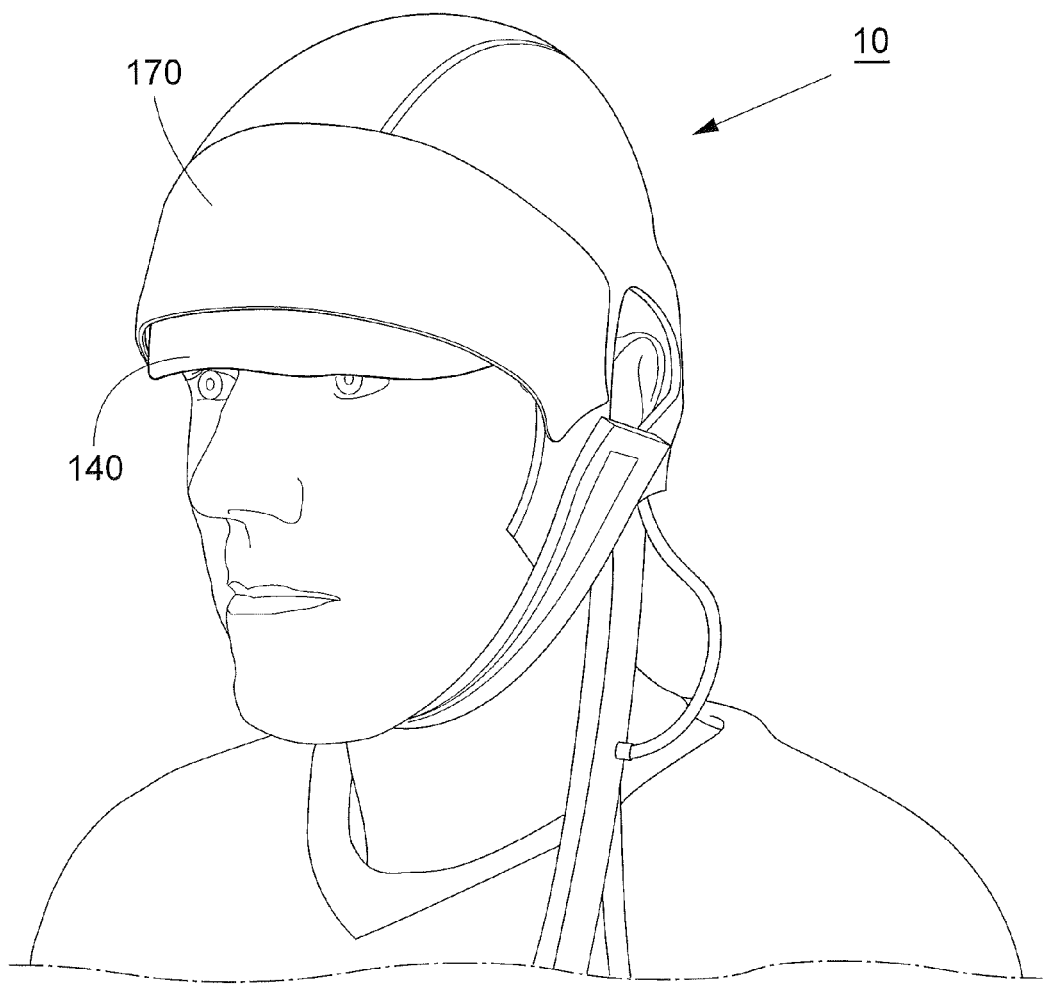
FIG. 18 shows the head cooler according to FIG. 17 with the insulating eyebrow cover in lowered position.

The eyebrow cooler can be used in combination with the head cooler as shown in FIGS. 17 and 18, or separately. FIG. 17 shows a patient having an eyebrow cooler 140 arranged tightly over the eyebrows and a head cooler 10 arranged on the head. The hoses 142 are arranged under the outer insulating cover 12. An eyebrow cooler cover 170 is provided to be arranged over the eyebrow cooler 140 for insulation against the surrounding air, and is shown in a raised position in FIG. 17 and in a lowered position in FIG. 18.

Holes, provided or not with valves, can be arranged into the cavity or the multiple cavities of the eyebrow cooler 140 for circulation and recirculation of the cooling fluid via external hoses in direct communication with the fluid source. Also, the eyebrow cooler can be filled with a cooling fluid before arranging it over the patient's eyebrows.

The head cooler described above is provided for use in medicine, and more specifically for preventing hair loss during chemotherapy treatment. A method for preventing hair loss on a patient is also provided by arranging the head cooler on the head of said patient.

Furthermore, the head cooler described above is provided for use in medicine, and more specifically for the treatment of patients suffered from stroke. The cooling of the head of stroke patients alleviates the damage caused by the stroke. A method for treatment of patients suffered from stroke is thus also provided by arranging the head cooler on the head of said patient.

In the claims, the term "comprises/comprising" does not exclude the presence of other elements or steps. Furthermore, although individually listed, a plurality of means, elements or method steps may be implemented. Additionally, although individual features may be included in different embodiments, these may possibly be combined in other ways, and the inclusion in different embodiments does not imply that a combination of features is not feasible.

In addition, singular references do not exclude a plurality. The terms "a", "an" does not preclude a plurality. Reference signs in the claims are provided merely as a clarifying example and shall not be construed as limiting the scope of the claims in any way.

The invention claimed is:

1. A method of treating a stroke patient suffering from stroke by cooling the stroke patient's head to alleviate damage caused by said stroke, the method comprising:
providing a cooling device comprising a thermal exchange cap to be arranged on the stroke patient's head, an adjustable heat exchange surface and at least one flow passage system forming the heat exchange surface, wherein the at least one flow passage system comprises at least one inlet and at least one outlet forming a single flow path in a front section of the cooling device between one inlet and one outlet, and wherein the thermal exchange cap comprises an opening constructed to receive a syringe for injecting heat conducting material;
applying the heat exchange surface directly against the stroke patient's head;
injecting a heat conducting material through the opening into the cap to adjust the fit of the cap, wherein the heat conducting material is selected from the group consisting of a gel, a hydrogel, a liquid, and a paste; and
flowing a cooling liquid in the at least one flow passage system,
wherein the heat exchange surface separates the stroke patient's head from the cooling liquid so that the cooling liquid does not contact the stroke patient's head during the step of flowing the cooling liquid,
and wherein the single flow path comprises a plurality of loops arranged to flow cooling liquid across the stroke patient's head in the front section of the cooling device.

2. The method according to claim 1, wherein said at least one flow passage system comprises at least two flow passage systems.

3. The method according to claim 1, further comprising the step of compensating for a discrepancy as to shape and size between the heat exchange surface and said head by adjusting the heat exchange surface.

4. The method according to claim 2, wherein said at least two flow passage systems comprise at least two inlets and at least one outlet connected to an external device for circulating said cooling fluid through said at least two flow passage systems; and wherein each flow passage system is provided with an inlet for independent provision of cooling liquid.

5. The method according to claim 2, wherein said at least two flow passage systems comprise a first flow passage system extending over a forward portion of said head and a second flow passage system extending over a neck portion of said head, wherein the entire heat exchange surface is covered by the at least two flow passage systems.

6. The method according to claim 5, wherein said first flow passage system extends over a forward portion of the thermal exchange cap and said second flow passage system extends over a neck portion of the thermal exchange cap, wherein the entire heat exchange surface is covered by the at least two flow passage systems.

7. The method of claim 1, wherein the each flow passage system comprises a flow passage that is meander shaped, labyrinth shaped, or maze shaped.

8. The method of claim 1, wherein the cooling device has a cooling capacity that is maximized by directing the flow of the cooling liquid into the flow passages through one or more inlets positioned in a posterior section of the cooling device and in a plane substantially perpendicular to an anterioposterior axis of the patient.

9. The method of claim 1, wherein the thermal exchange cap comprises a flexible elastic material and wherein the heat exchange surface can be adjusted for the size and shape of the patient's head.

10. The method of claim 2 further comprising flowing the cooling liquid at a different flow rate in a first flow passage system than in a second flow passage system.

11. The method of claim 2 further comprising providing a cooling liquid at a first temperature to a first flow passage and at a second temperature to a second flow passage, wherein the first temperature is different from the second temperature.

12. The method of claim 1 further comprising:
   monitoring the temperature of the patient's scalp with a temperature sensor operatively connected to an external circulating device for circulating the cooling liquid; and
   shutting off flow of cooling liquid when the temperature sinks below a temperature where frost injury is avoided.

13. The method of claim 1 further comprising inflating an inner head cover forming a lining on the inside of the thermal exchange cap and supplying cooling fluid into the inner head cover through a valve positioned between the inner head cover and a flow passage system.

* * * * *